United States Patent
Kojima et al.

(10) Patent No.: US 9,657,121 B2
(45) Date of Patent: May 23, 2017

(54) RUBBER COMPOSITION FOR TIRE, TIRE MEMBER, METHOD FOR PRODUCING BIOMASS-DERIVED RUBBER, AND PNEUMATIC TIRE

(71) Applicant: SUMITOMO RUBBER INDUSTRIES, LTD., Kobe-shi, Hyogo (JP)

(72) Inventors: Ryoji Kojima, Kobe (JP); Yuka Yokoyama, Kobe (JP)

(73) Assignee: SUMITOMO RUBBER INDUSTRIES, LTD., Kobe-Shi (JP)

( * ) Notice: Subject to any disclaimer, the term of this patent is extended or adjusted under 35 U.S.C. 154(b) by 0 days.

(21) Appl. No.: 14/413,665

(22) PCT Filed: Jul. 24, 2013

(86) PCT No.: PCT/JP2013/069984
§ 371 (c)(1),
(2) Date: Jan. 8, 2015

(87) PCT Pub. No.: WO2014/017508
PCT Pub. Date: Jan. 30, 2014

(65) Prior Publication Data
US 2015/0126698 A1    May 7, 2015

(30) Foreign Application Priority Data

Jul. 25, 2012  (JP) .................................. 2012-164948

(51) Int. Cl.
*C08F 136/06*  (2006.01)
*C08F 236/06*  (2006.01)
(Continued)

(52) U.S. Cl.
CPC .............. *C08F 136/06* (2013.01); *B60C 1/00* (2013.01); *C08F 236/06* (2013.01); *C08L 9/00* (2013.01);
(Continued)

(58) Field of Classification Search
CPC ........ C08F 136/06; C08F 236/06; C08L 9/00; C07C 11/167
See application file for complete search history.

(56) References Cited

U.S. PATENT DOCUMENTS

2010/0168312 A1  7/2010  Ishida et al.
2010/0216958 A1*  8/2010  Peters .................. C07D 333/48
                                                              526/258
(Continued)

FOREIGN PATENT DOCUMENTS

CN    101356223 A    1/2009
CN    102030933 A    4/2011
(Continued)

OTHER PUBLICATIONS

Derwent Abstract of WO 2009/125037 (Acc No. 2009-P82911, Oct. 2009).*
(Continued)

*Primary Examiner* — Brieann R Fink
(74) *Attorney, Agent, or Firm* — Birch, Stewart, Kolasch & Birch, LLP

(57) ABSTRACT

The present invention provides rubber compositions for tires capable of providing tire components and pneumatic tires having low-temperature properties and abrasion resistance that are equivalent to those of tire components and pneumatic tires formed from conventional synthetic rubber, respectively, while meeting the demand for a sound material-cycle society. The present invention relates to rubber compositions for tires containing a biomass-derived rubber
(Continued)

obtained by polymerizing a biomass-derived monomer component, the biomass-derived rubber having a pMC (percent modern carbon) value of 1% or greater as determined in conformity with ASTM D6866-10, and having a Tg (glass transition temperature) value of −120° C. to −80° C.

10 Claims, 1 Drawing Sheet

(51) Int. Cl.
    *C08L 9/00*     (2006.01)
    *C07C 11/167*     (2006.01)
    *B60C 1/00*     (2006.01)
    *C12P 5/02*     (2006.01)
    *C12P 7/16*     (2006.01)

(52) U.S. Cl.
    CPC ............... *C12P 5/02* (2013.01); *C12P 5/026* (2013.01); *C12P 7/16* (2013.01); C08L 2205/02 (2013.01); C08L 2205/025 (2013.01); Y02E 50/10 (2013.01)

(56) References Cited

U.S. PATENT DOCUMENTS

2011/0082234 A1* 4/2011 Hattori et al. ............... 523/150
2011/0114241 A1* 5/2011 Unseld et al. ............... 152/564
2011/0282000 A1* 11/2011 Hayes ........................... 524/553

FOREIGN PATENT DOCUMENTS

| ES | WO 2009125037 A1 * | 10/2009 | ............ C12P 7/06 |
|---|---|---|---|
| JP | 2003-63206 A | 3/2003 | |
| JP | 2011-32302 A | 2/2011 | |
| JP | 2011-38011 A | 2/2011 | |
| JP | 2011-74324 A | 4/2011 | |
| JP | 2011-79915 A | 4/2011 | |
| JP | 2011-140612 A | 7/2011 | |
| JP | 2011-140613 A | 7/2011 | |
| JP | 2011-526943 A | 10/2011 | |
| JP | 2013-241549 A | 12/2013 | |
| JP | 2013-241550 A | 12/2013 | |
| JP | 2013-249377 A | 12/2013 | |
| JP | 2013-249378 A | 12/2013 | |
| JP | 2013-249379 A | 12/2013 | |
| JP | 5638041 B2 | 10/2014 | |
| WO | WO 2010/078457 A | 7/2010 | |
| WO | WO 2010/099201 A | 9/2010 | |
| WO | WO 2010/071682 A1 | 6/2011 | |
| WO | WO 2011/085223 A1 | 7/2011 | |

OTHER PUBLICATIONS

International Search Report, issued in PCT/JP2013/069984, dated Oct. 29, 2013.

* cited by examiner

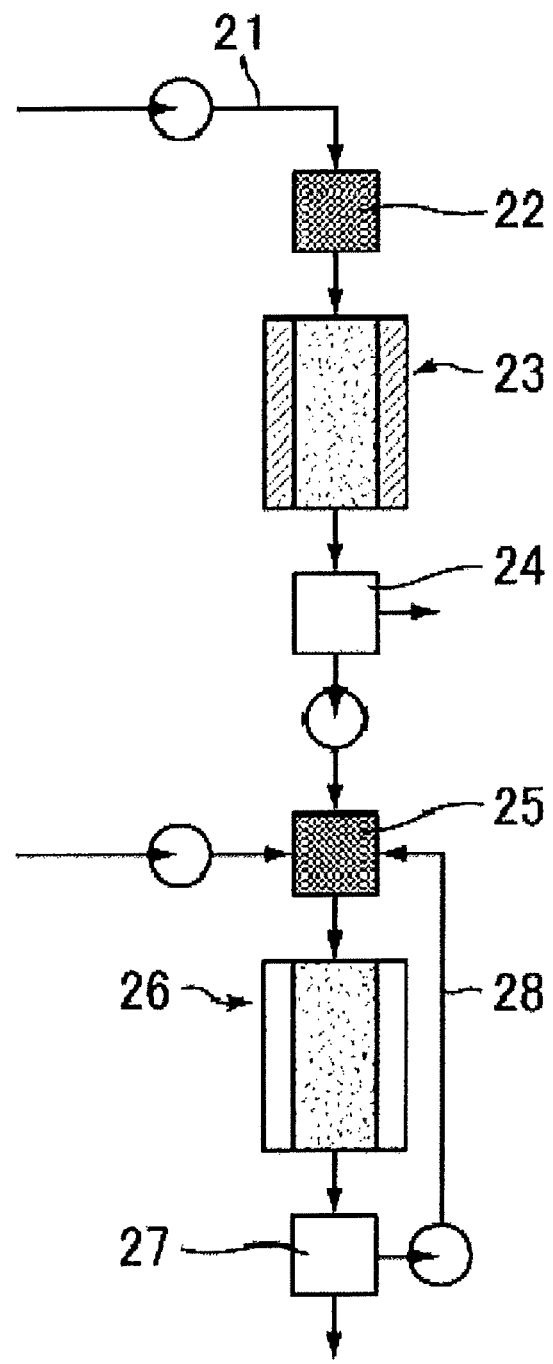

RUBBER COMPOSITION FOR TIRE, TIRE MEMBER, METHOD FOR PRODUCING BIOMASS-DERIVED RUBBER, AND PNEUMATIC TIRE

TECHNICAL FIELD

The present invention relates to rubber compositions for tires, and tire components and pneumatic tires formed from the rubber compositions.

BACKGROUND ART

Currently marketed tires are manufactured from materials derived from petroleum resources such that these materials account for half or more of the total weight of the tire. For example, common radial tires for passenger cars contain, based on the total weight of the tire, about 20% of synthetic rubber and about 20% of carbon black as well as aromatic oil and synthetic fibers. Thus, they contain at least 50% of petroleum-derived materials as a whole.

The recent emphasis on the environmental issues, however, has led to tighter $CO_2$ emission restrictions. Moreover, since petroleum raw material is a limited resource and the amount of the material supplied is decreasing year by year, oil prices are expected to escalate in the future and thus the use of petroleum-derived materials has a limit.

Hence, the people's desire to construct a sound material-cycle society has recently become stronger. Accordingly, there is a need for a departure from fossil fuel dependence in the material field as well as in the energy field, and the use of biomass has been focused on.

For example, Patent Literature 1 discloses an environment-friendly tire technology against a future decrease in petroleum supply, according to which a tire is formed in which 75% by weight or more of the total weight of the tire is made from materials derived from resources other than petroleum, for example, by replacing synthetic rubber with natural rubber, carbon black with inorganic filler or bio filler, petroleum oil with vegetable oil or fat, and synthetic fibers with natural fibers.

However, unfortunately, natural rubber is inferior in low-temperature properties and abrasion resistance to synthetic rubber such as polybutadiene rubber.

CITATION LIST

Patent Literature

Patent Literature 1: JP 2003-63206 A

SUMMARY OF INVENTION

Technical Problem

The present invention aims to solve the above problem by providing rubber compositions for tires capable of providing tire components and pneumatic tires having low-temperature properties and abrasion resistance that are equivalent to those of tire components and pneumatic tires formed from conventional synthetic rubber, respectively, while meeting the demand for a sound material-cycle society.

Solution to Problem

The present invention relates to rubber compositions for tires, comprising a biomass-derived rubber obtained by polymerizing a biomass-derived monomer component, the biomass-derived rubber having a pMC (percent modern carbon) value of 1% or greater as determined in conformity with ASTM D6866-10, and having a Tg (glass transition temperature) value of −120° C. to −80° C.

The monomer component is preferably at least one selected from the group consisting of butadiene, myrcene, ocimene, and cosmene.

The biomass-derived rubber is preferably a diene rubber.

Preferably, the monomer component forming the biomass-derived rubber comprises 50 mol % or more of butadiene.

Preferably, the biomass-derived rubber is obtained by polymerizing a diene prepared by catalytic reaction from at least one biomass-derived ingredient selected from the group consisting of biomass-derived alkyl alcohols, allyl alcohols, alkenes, aldehydes, and unsaturated carboxylic acids.

The at least one of the alkyl alcohols is preferably at least one selected from the group consisting of ethanol, butanol, and butanediol.

The butanol is preferably produced by at least one selected from the group consisting of microorganisms, plants, animals, and tissue cultures thereof, into which has been introduced at least one gene selected from the group consisting of mevalonate pathway-related genes, MEP/DOXP pathway-related genes, butyryl-CoA dehydrogenase encoding gene, butyl aldehyde dehydrogenase encoding gene, and butanol dehydrogenase encoding gene.

The at least one of the allyl alcohols is preferably at least one of crotyl alcohol and 3-buten-2-ol.

The at least one of the alkenes is preferably at least one of butene and ethylene.

The ethylene is preferably converted from biomass by fermentation using at least one selected from the group consisting of microorganisms, plants, animals, and tissue cultures thereof.

The at least one of the microorganisms, plants, animals, and tissue cultures thereof producing the ethylene preferably comprises an ACC synthase encoding gene that is introduced or modified, or modified and introduced.

The at least one of the aldehydes is preferably acetaldehyde.

The at least one of the unsaturated carboxylic acids is preferably at least one of tiglic acid and angelic acid.

The biomass-derived rubber is preferably obtained by polymerizing a monomer component which is directly produced from biomass by at least one selected from the group consisting of microorganisms, plants, animals, and tissue cultures thereof.

The monomer component is preferably at least one selected from the group consisting of butadiene, myrcene, ocimene, and cosmene.

Preferably, the monomer component is butadiene and the butadiene is converted from at least one selected from the group consisting of saccharides, hemiterpenes, and amino acids.

The at least one of the amino acids is preferably at least one selected from the group consisting of valine, leucine, isoleucine, and arginine.

Preferably, the at least one of the hemiterpenes and amino acids is converted into the butadiene by at least one enzyme selected from the group consisting of HMG-CoA reductase, diphosphomevalonate decarboxylase, and amino acid decarboxylases.

Preferably, the monomer component is butadiene, and the at least one of the microorganisms, plants, animals, and tissue cultures thereof producing the butadiene comprises at least one gene selected from the group consisting of HMG-CoA reductase encoding gene, diphosphomevalonate decarboxylase encoding gene, and amino acid decarboxylase encoding genes, that is introduced or modified, or modified and introduced.

The biomass-derived rubber is preferably a polybutadiene rubber formed from biomass-derived butadiene by an enzymatic reaction.

The enzymatic reaction is preferably catalyzed by a long prenyl chain elongating enzyme.

The biomass-derived rubber is preferably a polybutadiene rubber produced by tissue culturing at least one selected from the group consisting of microorganisms, plants, and animals.

Preferably, a saccharide content based on 100% by mass of the biomass is 20% by mass or more.

Preferably, a combined content of amino acid and protein based on 100% by mass of the biomass is 10% by mass or more.

Preferably, a combined content of fatty acid and fatty acid ester based on 100% by mass of the biomass is 10% by mass or more.

Preferably, the biomass-derived rubber is obtained by polymerizing the biomass-derived monomer component that comprises a combination of differently derived monomers.

The biomass-derived rubber is preferably obtained by polymerizing the biomass-derived monomer component and a petroleum-derived monomer component.

The biomass-derived rubber is preferably obtained by polymerizing the biomass-derived monomer component or a combination of the biomass-derived monomer component and a petroleum-derived monomer component, at an appropriately chosen ratio depending on at least one of biomass resource supply situation, petroleum resource supply situation, and market needs.

The present invention also relates to rubber compositions for tires, comprising a polybutadiene rubber, the polybutadiene rubber being polymerized from butadiene starting material at least part of which is obtained by a reaction or a series of reactions starting from biomass.

The present invention also relates to a method of producing a biomass-derived rubber having a pMC (percent modern carbon) value of 1% or more as determined in conformity with ASTM D6866-10, and having a Tg (glass transition temperature) value of −120° C. to −80° C., the method comprising polymerizing a biomass-derived monomer component or a combination of a biomass-derived monomer component and a petroleum-derived monomer component, at an appropriately chosen ratio depending on at least one of biomass resource supply situation, petroleum resource supply situation, and market needs.

The present invention also relates to tire components, which are formed from the rubber compositions.

The present invention also relates to pneumatic tires, which are formed from the rubber compositions.

Advantageous Effects of Invention

The rubber compositions for tires according to the present invention contain a biomass-derived rubber obtained by polymerizing a biomass-derived monomer component, the biomass-derived rubber having a percent modern carbon (pMC) determined in conformity with ASTM D6866-10 of 1% or greater and a glass transition temperature (Tg) of −120° C. to −80° C. Thus, they can exhibit good low-temperature properties, abrasion resistance, and flex fatigue resistance that are equivalent to those when conventional synthetic rubber is used, while meeting the demand for a sound material-cycle society. Therefore, these rubber compositions can provide tire components and pneumatic tires having low-temperature properties, abrasion resistance, and flex fatigue resistance that are equivalent to those of tire components and pneumatic tires formed from conventional synthetic rubber, respectively, while meeting the demand for a sound material-cycle society.

BRIEF DESCRIPTION OF DRAWINGS

FIG. 1 is a schematic view simply showing a system for producing butadiene.

DESCRIPTION OF EMBODIMENTS

The rubber compositions for tires of the present invention contain a biomass-derived rubber obtained by polymerizing a biomass-derived monomer component, the biomass-derived rubber having a percent modern carbon (pMC) determined in conformity with ASTM D6866-10 of 1% or greater and a glass transition temperature (Tg) of −120° C. to −80° C.

The rubber component used in the present invention includes a biomass-derived rubber which is obtained by polymerizing a biomass-derived monomer component and which has a pMC value of 1% or greater as determined in conformity with ASTM D6866-10 and also has a Tg (glass transition temperature) value of −120° C. to −80° C.

The pMC value refers to a ratio of the $^{14}C$ content in a sample to that of a modern reference standard (modern standard reference). In the present invention, this value is used as an index of the percentage of biomass in a compound (rubber). The following will describe what this value means.

One mole of carbon atoms ($6.02 \times 10^{23}$ carbon atoms) includes about $6.02 \times 10^{11}$ $^{14}C$ atoms (about one trillionth of the number of normal carbon atoms). $^{14}C$ is called a radioactive isotope and its half-life period is 5730 years and the number thereof regularly decreases. Decay of all the $^{14}C$ atoms requires 226,000 years. In other words, in the fossil fuels, such as coal, petroleum, and natural gas, which are considered to be at 226,000 years or longer after carbon dioxide and the like in the air were taken into and fixed in plants and the like, all the $^{14}C$ atoms which had been contained therein at the beginning of fixation are decayed. Thus, in the current 21st century, fossil fuels, such as coal, petroleum, and natural gas, contain no $^{14}C$ atoms. Accordingly, chemical substances prepared from such fossil fuel materials contain no $^{14}C$ atoms either.

Meanwhile, $^{14}C$ is unceasingly generated by nuclear reaction of cosmic rays in the atmosphere and this generation balances with the $^{14}C$ reduction due to radioactive decay. Thus, in the global atmosphere, the amount of $^{14}C$ is constant. Then, the $^{14}C$ content in substances derived from biomass resources which are being cycled in the current environment is about $1 \times 10^{-12}$ mol % of the total C atom content as described above. Such a difference between the contents permits calculation of the percentage of compounds derived from natural resources (compounds derived from biomass resources) (biomass ratio) in a certain compound (rubber).

The amount of $^{14}C$ is usually determined as follows. $^{13}C$ content ($^{13}C/^{12}C$) and $^{14}C$ content ($^{14}C/^{12}C$) are determined using tandem accelerator mass spectrometry. In the determination, the $^{14}C$ content in the natural carbon cycle at 1950 is used as a modern standard reference, that is, a standard $^{14}$C content. The specific standard substance used is an oxalic acid standard offered by the National Institute of Standards and Technology (NIST), United States. The specific radioactivity of carbon (radioactivity of $^{14}$C per gram of carbon) in the oxalic acid is corrected for carbon isotopic fractionation to a certain value for $^{13}$C, and then corrected for decay between 1950 AD to the measurement date. This corrected value is taken as a standard $^{14}$C content (100%). The ratio between this value and the actual measurement value of a sample is defined as pMC in the present invention.

Accordingly, a rubber formed from 100% materials derived from biomass (natural materials) is expected to have about 110 pMC although there are some differences such as regional differences (currently, such substances often fail to exhibit a value of 100 in usual conditions). On the other hand, the $^{14}$C content of chemical substances derived from fossil fuels, such as petroleum, is expected to be substantially 0 pMC (for example, 0.3 pMC). This value corresponds to a biomass ratio of 0% as mentioned above.

Thus, rubbers with high pMC, in other words, rubbers with a high biomass ratio can be suitably used in rubber compositions for tires in view of environmental protection.

The biomass-derived rubber has a pMC value of 1% or greater, preferably 10% or greater, more preferably 50% or greater, and still more preferably 100% or greater as determined in conformity with ASTM D6866-10 (this pMC value indicates the biomass ratio of the biomass-derived rubber). The upper limit thereof is not particularly limited. The pMC is preferably as great as possible in order to more meet the demand for a sound material-cycle society. As mentioned above, since pMC is by its very nature calculated as a ratio to a standard substance, it may possibly be a value exceeding 100%.

In the present invention, the pMC values of rubbers (biomass-derived rubbers) are determined in conformity with ASTM D6866-10, and specifically by the method described in EXAMPLES.

As described in EXAMPLES, $^{14}$C content analysis of rubbers requires pretreatment of the rubbers. Specifically, all the carbon atoms contained in a rubber are oxidized and converted into carbon dioxide. Further, after the resulting carbon dioxide is separated from water and nitrogen, the carbon dioxide needs to be reduced and converted into graphite, which is solid carbon. Then, the resulting graphite is irradiated with cations such as Cs$^+$ so that carbon anions are generated. The carbon ions are accelerated using a tandem accelerator so that the anions are converted into cations by charge exchange reaction. The orbitals of $^{12}$C$^{3+}$, $^{13}$C$^{3+}$, and $^{14}$C$^{3+}$ are separated using a mass analysis electromagnet, and $^{14}$C$^{3+}$ can be measured with an electrostatic analyzer.

The biomass-derived rubber has a glass transition temperature (Tg) of −120° C. to −80° C. The rubber having a Tg value falling within this range can provide tires with low-temperature properties (e.g. grip performance on snow and grip performance on ice) at levels that have not been achieved by conventionally used natural rubber (100% biomass-derived rubber). The Tg value is preferably −90° C. or lower, more preferably −95° C. or lower, and still more preferably −100° C. or lower. If the Tg value is higher than −80° C., low-temperature properties tend to decrease. The Tg value is also preferably −115° C. or higher. Rubbers having a Tg value of lower than −120° C. are difficult to produce and may not be suitably used in many purposes.

In the present invention, the Tg of rubbers (biomass-derived rubbers) can be determined by the method described in EXAMPLES.

As mentioned above, the present invention uses, in rubber compositions for tires, a biomass-derived rubber which has a specific glass transition temperature in spite of having a specific pMC value or greater. Thus, the present invention can solve the problem which is not solved by conventional techniques, in other words, the present invention can provide tire components and pneumatic tires having low-temperature properties and abrasion resistance that are equivalent to or better than those of tire components and pneumatic tires formed from conventional synthetic rubber, respectively, while meeting the demand for a sound material-cycle society.

The biomass-derived rubber is preferably a myrcene polymer or a diene rubber, and more preferably a diene rubber. For good low-temperature properties and good abrasion resistance, it is still more preferably a polybutadiene rubber (biomass polybutadiene rubber (BBR)).

The diene rubber may contain structural units derived from monomers other than diene monomers (copolymerizable monomers such as aromatic diene monomers (e.g. styrene) and monoterpenes (e.g. myrcene)), as long as it satisfies the above pMC range and the above Tg range.

The BBR may contain structural units derived from monomers other than butadiene (copolymerizable monomers such as diene monomers (e.g. isoprene) other than butadiene, aromatic diene monomers (e.g. styrene), and monoterpenes (e.g. myrcene)), as long as it satisfies the above pMC range and the above Tg range.

For good abrasion resistance and good flex fatigue resistance, the BBR preferably has a cis content of 70% by mass or more, more preferably 80% by mass or more, and still more preferably 90% by mass or more.

The cis content in BBR can be determined by the method described in EXAMPLES.

For good abrasion resistance and good flex fatigue resistance, the BBR preferably has a weight average molecular weight (Mw)/number average molecular weight (Mn) ratio of 1 to 10, and more preferably 1 to 5.

The Mw and the Mn of BBR can be determined by the method described in EXAMPLES.

The biomass-derived rubber is obtained by polymerizing a biomass-derived monomer component.

The rubber obtained by polymerizing a biomass-derived monomer component in the present invention includes not only rubbers obtained by polymerizing a biomass-derived monomer component in accordance with conventional methods but also rubbers formed by reactions with microorganisms, plants, animals, and tissue cultures thereof (hereinafter, also referred to as microorganisms and the like) or by enzymatic reactions.

The biomass is also referred to as biomass resource in the present invention.

The biomass (biomass resource) herein means carbon-neutral organic resources derived from organisms, and specific examples thereof include: those converted into starch, cellulose or the like and stored; bodies of animals which eat plants to grow up; and products of processed plant or animal bodies, but exclude fossil resources.

The biomass resource may be edible or nonedible and is not particularly limited. In consideration of effective use of resources without competing with the demand as food, the biomass resource is preferably a nonedible material.

Specific examples of the biomass resource include cellulose products (e.g. pulp, kenaf, straw, rice straw, wastepaper, and papermaking residues), wood, charcoal, compost, natural rubber, cotton, sugar cane, soy pulp, fats and oils (e.g. rapeseed oil, cottonseed oil, soybean oil, coconut oil, and castor oil), hydrocarbon products (e.g. corn, tubers, wheat, rice, chaff, rice bran, old rice, cassava, and sago palm), bagasse, buckwheat, soybean, essential oils (e.g. pine root oil, orange oil, and eucalyptus oil), black liquor, kitchen garbage, waste vegetable oils, residues of aquatic products, livestock waste, food waste, algae, and drainage sludge.

The biomass resource may be any of products obtained by treating the above resources (i.e., biomass-derived materials). The treatment may be carried out for example by known methods, such as biological treatments based on, for example, the activities of microorganisms, plants, animals, and tissue cultures thereof; chemical treatments using, for example, acids, alkalis, catalysts, thermal energy, and light energy; and physical treatments such as milling, compression, microwave treatment, and electromagnetic treatment.

The biomass resource may be any of those which are refined or extracted from the aforementioned biomass resources or treated biomass resources (i.e., biomass-derived materials). For example, the biomass resource may be any of saccharides, proteins, amino acids, fatty acids, fatty acid esters, and others which are refined from biomass resources.

The saccharide may be any biomass-derived one, and examples thereof include sucrose, glucose, trehalose, fructose, lactose, galactose, xylose, allose, talose, gulose, altrose, mannose, idose, arabinose, apiose, maltose, cellulose, starch, and chitin.

The protein may be any biomass-derived compound that is formed by linking amino acids (preferably L-amino acids), and include oligopeptides such as dipeptides.

The amino acid may be any biomass-derived organic compound having both amino and carboxyl functional groups. Examples thereof include valine, leucine, isoleucine, arginine, lysine, asparagine, and glutamine. Preferred among these are valine, leucine, isoleucine, and arginine. The amino acid may be an L-amino acid or a D-amino acid, but it is preferably an L-amino acid because it is present in a large amount in nature and is easy to use as a biomass resource.

The fatty acid may be any biomass-derived one, and examples thereof include butyric acid, oleic acid, linoleic acid, palmitic acid, and stearic acid.

The fatty acid ester may be any biomass-derived one, and examples thereof include animal-derived fats, vegetable oils, and modified biomass-derived fats and oils.

The biomass resource may contain various materials and impurities. For efficient conversion, however, the saccharide content based on 100% by mass of the biomass is preferably 20% by mass or more, more preferably 30% by mass or more, and still more preferably 50% by mass or more. In another embodiment, for efficient conversion, the combined content of amino acid and protein based on 100% by mass of the biomass is preferably 10% by mass or more, more preferably 20% by mass or more, and still more preferably 30% by mass or more. In yet another embodiment, for efficient conversion, the combined content of fatty acid and fatty acid ester based on 100% by mass of the biomass is preferably 10% by mass or more.

The biomass-derived monomer component may include, for example, butadiene; monoterpenes such as myrcene, ocimene, and cosmene; hemiterpenes such as tiglic acid and angelic acid; sesquiterpenes; squalenes; diterpenes; and carotenoids. Preferred among these are butadiene (1,3-butadiene), myrcene (β-myrcene), ocimene (β-ocimene), and cosmene. For good low-temperature properties and good abrasion resistance, butadiene (1,3-butadiene) is more preferred.

The myrcene can be extracted from laurel or verbena, the ocimene can be extracted from lavender or Lima bean, and the cosmene can be extracted from cosmos, for example.

For good low-temperature properties and good abrasion resistance, the butadiene content based on 100 mol % of the monomer component forming the biomass-derived rubber is preferably 50 mol % or more, more preferably 70 mol % or more, still more preferably 80 mol % or more, particularly preferably 90 mol % or more, and most preferably 95 mol % or more. This content may be 100 mol %.

The following representative example specifically describes the case where the biomass-derived rubber is BBR obtained by polymerizing biomass-derived butadiene. As mentioned above, the BBR obtained by polymerizing biomass-derived butadiene in the present invention includes not only BBRs obtained by polymerizing biomass-derived butadiene by conventional methods but also BBRs formed by reactions with microorganisms and the like or by enzymatic reactions.

Butadiene may be prepared from biomass resources by any of various methods. Examples thereof include: biological treatments in which butadiene is directly prepared from biomass resources using at least one selected from the group consisting of microorganisms, plants, animals, and tissue cultures thereof; methods of performing the aforementioned chemical treatments on biomass resources to form butadiene; methods of performing the aforementioned physical treatments on biomass resources to form butadiene; methods of converting biomass resources into butadiene by in-vitro enzymatic reactions or the like; and any combination of these methods. The at least one of the microorganisms, plants, and animals which convert biomass resources into butadiene may or may not be genetically engineered.

Biomass resources may directly be converted into butadiene using microorganisms and the like by any method, and the conversion may be carried out using an in-vivo pathway which converts an amino acid into an alkyl alcohol and/or a hemiterpene.

The amino acid is preferably valine, leucine, isoleucine, or arginine. Moreover, the hemiterpene is preferably tiglic acid and/or angelic acid.

Preferably, butadiene may be prepared from an amino acid and/or a hemiterpene using a microorganism, plant, animal, or a tissue culture thereof which has a gene encoding an enzyme having a decarboxylase activity and/or a gene encoding an enzyme having a reductase activity that are introduced and/or modified.

Examples of the enzymes having a decarboxylase activity include diphosphomevalonate decarboxylase (EC 4.1.1.33) and various amino acid decarboxylases. Examples of the enzymes having a reductase activity include HMG-CoA reductase and 12-oxophytodienoate reductase (EC 1.3.1.42).

Preferred methods of producing butadiene by fermentation through an amino acid-mediated in-vivo reaction include methods of producing butadiene by reacting any of various decarboxylases with tiglic acid and/or angelic acid, which are synthesized in vivo from isoleucine through natural metabolic pathways of microorganisms and the like. Alternatively, butadiene may be prepared by decarboxylase reactions using various fatty acid derivatives which are produced during amino acid metabolism.

The amino acid required for preparing butadiene may directly be added to a medium. It is preferred to use a biosynthetic amino acid synthesized in vivo by fermentation of a ground plant, a livestock waste or the like. In this case, polybutadiene rubber is converted from a saccharide and/or a protein.

Usual methods of producing alcohols or alkenes by fermentation mainly utilize saccharides as biomass resources; in contrast, the above production methods have great potential to effectively utilize biomass resources mainly containing amino acids and proteins and thus are useful.

Other preferred methods of preparing butadiene from biomass resources include methods in which an intermediate capable of being used to synthesize butadiene is prepared from a biomass resource using at least one selected from the group consisting of microorganisms, plants, animals, and tissue cultures thereof, and the resulting intermediate is then subjected to, for example, the aforementioned chemical treatment, such as catalytic reaction, the aforementioned physical treatment, the aforementioned in-vitro enzymatic reaction, or any combination of these methods to form butadiene (dienes such as butadiene).

Examples of the intermediates capable of being used to synthesize butadiene include alkyl alcohols, allyl alcohols, alkenes, aldehydes, and unsaturated carboxylic acids.

The alkyl alcohol may be any biomass-derived one, and is preferably ethanol, butanol, or butanediol, and more preferably butanol or butanediol. The butanol may be 1-butanol or 2-butanol or a mixture thereof.

Various methods are known to produce ethanol (biomass resource-derived ethanol is also referred to as bioethanol) or butanol (biomass resource-derived butanol is also referred to as biobutanol) from biomass resources by fermentation using microorganisms and the like. Typical examples thereof include a method of producing bioethanol from a biomass resource (e.g. sugar cane or glucose) by the fermentation of ethanol by yeast and a method of producing biobutanol from a biomass resource (e.g. glucose) by the fermentation of acetone and butanol (ABE fermentation) by fermentative microbes. In the ABE fermentation method, a solvent mixture of butanol, acetone, and others is obtained, and this mixture can be distilled off to provide biobutanol. Alternatively, butanol may be prepared directly from bioethanol by catalytic reaction, or may be prepared via acetaldehyde.

The ABE fermentation microorganism may be any microorganism capable of ABE fermentation. Examples thereof include microorganisms belonging to the genera *Escherichia, Zymomonas, Candida, Saccharomyces, Pichia, Streptomyces, Bacillus, Lactobacillus, Corynebacterium, Clostridium*, and *Saccharomyces*. These microorganisms may be any strains including wild-type and mutant strains, and recombinant strains induced by genetically engineering techniques, such as cell fusion or gene manipulation. Preferred among these are microorganisms belonging to the genus *Clostridium*, and more preferred are *Clostridium acetobutylicum, Clostridium beijerinckii, Clostridium saccharobutylicum*, and *Clostridium saccharoperbutylacetonicum*.

For example, a preferred method of producing biobutanol is to produce butanol by fermentation using at least one selected from the group consisting of microorganisms, plants, animals, and tissue cultures thereof, into which has been introduced at least one gene selected from the group consisting of mevalonate pathway-related genes, MEP/DOXP pathway-related genes, butyryl-CoA dehydrogenase encoding gene, butyl aldehyde dehydrogenase encoding gene, and butanol dehydrogenase encoding gene (for example, see JP 2010-508017 T).

The ethanol and butanol produced by fermentation of biomass resources are also commercially available as bioethanol and biobutanol (e.g., biobutanol of Du Pont), respectively.

Moreover, various fermentative methods of directly preparing butanediol as material for bioplastics are developed (for example, Syu M. J., Appl. Microbial Biotechnol. 55:10-18 (2001); Qin et al, Chinese J. Chem. Eng. 14(1):132-136 (2006); JP 2011-522563 T; JP S62-285779 A; and JP 2010-115116 A), and such butanediol can easily be used as bio-derived butanediol. The butanediol may also be prepared by conversion of biomass-derived succinic acid, fumaric acid, furfural, or the like.

The butanediol fermentation microorganism may be any microorganism capable of butanediol fermentation. Examples thereof include microorganisms belonging to the genera *Escherichia, Zymomonas, Candida, Saccharomyces, Pichia, Streptomyces, Bacillus, Lactobacillus, Corynebacterium, Clostridium, Klebsiella*, and *Saccharomyces*. These microorganisms may be any strains including wild-type and mutant strains, and recombinant strains induced by genetically engineering techniques, such as cell fusion or gene manipulation. Preferred among these are microorganisms belonging to the genera *Bacillus, Clostridium*, and *Klebsiella*, and more preferred are *Clostridium autoethanogenum, Bacillus polymyxa, Bacillus subtilis, Bacillus pumilus, Bacillus macerans, Bacillus licheniformis, Bacillus megaterium*, and *Klebsiella pneumoniae*.

The alkyl alcohol may be converted into butadiene for example by the aforementioned biological treatments, such as fermentation, the aforementioned chemical treatments, such as catalytic reaction, the aforementioned physical treatments, the aforementioned in-vitro enzymatic reactions, or any combination of these methods.

For direct conversion of the alkyl alcohol into butadiene, for example, a method is known in which ethanol and/or butanol is converted into butadiene using a dehydration or dehydrogenation catalyst, such as hydroxyapatite, $Ta/SiO_2$, alumina, or zeolite.

The allyl alcohol may be any biomass-derived one. For easy conversion into butadiene, crotyl alcohol and 3-buten-2-ol are preferred.

The crotyl alcohol and 3-buten-2-ol may directly be produced from biomass resources by fermentation using microorganisms and the like, or may be prepared by reducing biomass-derived crotonic acid or its derivatives. Also, the crotyl alcohol may be prepared from biomass-derived butanediol using a catalyst, such as zeolite, alumina, or cerium oxide (for example, see JP 2004-306011 A).

For conversion of the allyl alcohol into butadiene, mention may be made of a method of converting crotyl alcohol into butadiene by dehydration using a commonly known catalytic reduction catalyst, such as zeolite or alumina.

The alkene may be any biomass-derived one, and preferred are ethylene and butene (also referred to as butylene), with ethylene being more preferred.

The biomass-derived ethylene and butene may be prepared, for example, by a method of converting bioethanol into ethylene using a dehydration catalyst (e.g. alumina and zeolite) or by high-temperature treatment, and a method of converting biobutanol into butene using a dehydration catalyst (e.g. alumina and zeolite) or by high-temperature treatment, respectively.

These alkenes (ethylene and butene) can also directly be produced from biomass resources by fermentation using at least one selected from the group consisting of microorganisms, plants, animals, and tissue cultures thereof.

In preferred, but nonlimiting, embodiments, in view of productivity, the at least one of the ethylene fermentation microorganisms, plants, animals, and tissue cultures thereof has a gene encoding an enzyme having an ACC synthase (ethylene synthase) activity that is introduced and/or modified.

In preferred, but nonlimiting, embodiments, the at least one of the butene fermentation microorganisms, plants, animals, and tissue cultures thereof has a gene encoding an enzyme having a diphosphomevalonate decarboxylase (EC 4.1.1.33) activity that is introduced and/or modified (for example, see JP 2011-526489 T).

For conversion of the alkene into butadiene, mention may be made, for example, of: a method of converting butene into butadiene using alumina, zeolite, or the like; and a method of partially converting ethylene into acetaldehyde using an oxidation catalyst such as palladium chloride or palladium acetate, and then subjecting the acetaldehyde to a dehydration reaction with the remaining ethylene using a dehydration catalyst such as alumina or zeolite to form butadiene.

The aldehyde may be any biomass-derived one, and is preferably acetaldehyde.

The acetaldehyde may directly be produced from biomass resources by fermentation using microorganisms and the like, or may be converted from biomass-derived ethylene using an oxidation catalyst such as palladium chloride.

For conversion of the aldehyde into butadiene, mention may be made of a method including a dehydration reaction with ethylene, for example.

The unsaturated carboxylic acid may be any biomass-derived one, and tiglic acid and angelic acid are preferred.

The tiglic acid and angelic acid may directly be produced from biomass resources by fermentation using microorganisms and the like. Specifically, tiglic acid and angelic acid can be synthesized in vivo from isoleucine through natural metabolic pathways of microorganisms and the like. Alternatively, they may be refined from croton oil or the like.

For conversion of the unsaturated carboxylic acid into butadiene, mention may be made, for example, of: methods of reacting any of various decarboxylases with tiglic acid and/or angelic acid to cause conversion; and methods including reaction with metal catalysts (e.g. palladium), zeolite, alumina or the like to cause conversion.

The method of producing polybutadiene rubber (biomass polybutadiene rubber (BBR)) by polymerizing butadiene that is obtained from a biomass resource by any of the aforementioned methods may be similar to, but not limited to, any of the methods of producing polybutadiene rubber by polymerizing petroleum-derived butadiene which are known to the skilled person.

In view of easy availability, the performance of the resulting BBR, and others, the butadiene obtained from a biomass resource may suitably be butadiene derived from an alkyl alcohol (preferably ethanol or butanol, and more preferably butanol), butadiene derived from an alkene (preferably ethylene), or butadiene derived from an unsaturated carboxylic acid (preferably tiglic acid). It may also suitably be a combination of these butadienes.

The molecular weight, branching, and microstructure of the resulting BBR can appropriately be chosen by adjusting the polymerization conditions in accordance with conventionally known methods, depending on the desired tire performance. Moreover, the butadiene may be copolymerized with other monomers (copolymerizable monomers such as diene monomers other than butadiene (e.g., isoprene), aromatic diene monomers (e.g. styrene), and monoterpenes (e.g. myrcene)) at appropriate ratios (provided that the ratios must satisfy the pMC and Tg ranges mentioned above). The butadiene obtained from a biomass resource may also be used together with another butadiene (petroleum-derived butadiene) which is not butadiene obtained from a biomass resource.

Currently, there are some plans to develop biomass industrial complexes mainly for bioethanol, bioethylene, and the like. Bioethanol and bioethylene are produced mainly from saccharides and/or celluloses as biomass resources, and the effective use of other biomass resources, such as proteins, lipids, and amino acids, has not been achieved. In addition, the use of saccharides leads to competition with the demand as food and the overharvesting of celluloses leads to deforestation; therefore, a situation that is not necessarily environment-friendly may be caused.

Thus, the biomass-derived monomer component is preferably used in the form of a combination of multiple biomass-derived monomers, or a combination of the biomass-derived monomer component and a petroleum-derived monomer component, or a combination of these monomer components at an optimally adjusted ratio, depending on the comprehensive environmental needs, including the situation of supplying various biomass resources, the petroleum resource supply situation, and market needs (e.g. the trend of competition with the demand for biomass resources as food). This allows effective use of a wide variety of biomass resources such as saccharides, proteins, and lipids, without dependence on a single biomass resource, thus resulting in stable supply of biomass-derived rubber and attention to the environment according to the situation at the time of production. For example, biomass-derived butadiene can be prepared from the aforementioned various substrates such as bioethanol, biobutanol, and terpenes.

When the biomass-derived monomer component is a combination of multiple biomass-derived monomers, the monomers are preferably derived from different biomass species, in other words, monomers obtained from different biomass resources. This allows effective use of multiple biomass resources and thus more suitably meets the aforementioned comprehensive environmental needs.

Another preferred method of converting the butadiene obtained from a biomass resource into BBR involves an enzymatic reaction. Some enzymes (long prenyl chain elongating enzymes) contained in rubber latex are known to have an effect of promoting the diene polymerization reaction. These enzymes can be used in the polymerization in vivo or in vitro.

The long prenyl chain elongating enzyme may be any conventionally known one.

BBR may directly be prepared from biomass resources, for example, by a method of culturing (tissue culturing) at least one selected from the group consisting of microorganisms, plants, animals, and tissue cultures thereof, which are capable of diene polymerization, to directly convert a biomass resource into BBR; or a method of culturing at least one selected from the group consisting of microorganisms, plants, animals, and tissue cultures thereof in a medium containing butadiene (preferably butadiene obtained from a biomass resource) to polymerize BBR.

Suitable examples of the microorganisms and the like which are capable of diene polymerization include plants such as *Hevea brasiliensis, Ficus elastica*, the genus *Taraxacum, Ficus carica, Sonchus oleraceus, Solidago canadensis, Parthenium argentatum* Gray, *Manilkara zapota*, and *Eucommia ulmoides*, and tissue cultures thereof.

In culturing the microorganisms and the like, saccharides such as glucose are usually used as carbon sources. Thus, all the compounds produced by the microorganisms and the like correspond to biomass resource-derived materials.

As described above, BBR is polymerized from butadiene starting material (butadiene monomer) at least part of which is obtained by a reaction starting from biomass (a one-step reaction starting from a biomass resource to butadiene (reaction of directly generating butadiene from a biomass resource)) or by a series of reactions starting from biomass (a series of reactions of generating butadiene using a biomass resource as a starting material).

The biomass-derived rubber (preferably BBR) content based on 100% by mass of the rubber component is preferably 20% by mass or more, and more preferably 30% by mass or more. The upper limit of the content is not particularly limited and it is preferably 80% by mass or less, and more preferably 70% by mass or less. The biomass-derived rubber (preferably BBR) in an amount falling within the range mentioned above can provide good low-temperature properties, abrasion resistance, and flex fatigue resistance.

Examples of rubbers which can be used in the rubber component of the rubber composition for tires, other than the biomass-derived rubber include natural rubber (NR), epoxidized natural rubber (ENR), and synthetic diene rubber (e.g. polyisoprene rubber (IR), polybutadiene rubber (BR), styrene-butadiene rubber (SBR), styrene-isoprene-butadiene rubber (SIBR), chloroprene rubber (CR), acrylonitrile-butadiene rubber (NBR), ethylene-propylene-diene rubber (EPDM), butyl rubber (IIR), and halogenated butyl rubber (X-IIR)). These rubbers may be used alone or in combination of two or more. NR is preferred among these because its combined use with the biomass-derived rubber can provide good low-temperature properties, abrasion resistance, and flex fatigue resistance while meeting the demand for a sound material-cycle society.

The NR content based on 100% by mass of the rubber component is preferably 20% by mass or more, and more preferably 30% by mass or more. The content is also preferably 80% by mass or less, and more preferably 70% by mass or less. NR in an amount falling within the range mentioned above can provide good low-temperature properties, fuel economy, abrasion resistance, and flex fatigue resistance while meeting the demand for a sound material-cycle society.

The rubber compositions of the present invention preferably contain filler. The filler may be any conventionally known one used in tires. Examples of the filler include silica, carbon black, aluminum hydroxide, clay, calcium carbonate, montmorillonite, cellulose, glass balloons, and various staple fibers. In view of tire physical properties, the filler is preferably silica, carbon black, or aluminum hydroxide. These fillers may be used alone or in combination of two or more.

The amount of filler per 100 parts by mass of the rubber is preferably 10 to 200 parts by mass, more preferably 20 to 180 parts by mass, and still more preferably 30 to 150 parts by mass. Less than 10 parts by mass of filler tends to provide insufficient strength to the resulting rubber composition, resulting in reduced abrasion resistance and reduced flex fatigue resistance. Also, more than 200 parts by mass of filler tends to insufficiently disperse in the rubber, resulting in a reduction in rubber physical properties (i.e. fuel economy, abrasion resistance, and flex fatigue resistance).

The rubber compositions preferably contain silica, among the fillers, for improvement of the resulting tire in terms of fuel economy.

The silica preferably has a nitrogen adsorption specific surface area ($N_2SA$) determined by the BET method of 50 $m^2/g$ or greater, more preferably 100 $m^2/g$ or greater. If the $N_2SA$ is smaller than 50 $m^2/g$, rubber strength tends to be reduced and abrasion resistance and flex fatigue resistance also tend to be reduced. The $N_2SA$ is preferably 250 $m^2/g$ or smaller, and more preferably 200 $m^2/g$ or smaller. If the $N_2SA$ exceeds 250 $m^2/g$, processability tends to deteriorate and fuel economy, abrasion resistance, and flex fatigue resistance tend to deteriorate.

The $N_2SA$ values of silicas are determined by the BET method in conformity with ASTM D3037-93.

The amount of silica per 100 parts by mass of the rubber component is preferably 5 parts by mass or more, and more preferably 15 parts by mass or more. The amount of silica is preferably 200 parts by mass or less, more preferably 150 parts by mass or less, still more preferably 100 parts by mass or less, and particularly preferably 50 parts by mass or less. Silica in an amount falling within the range mentioned above can provide not only good fuel economy but also a good reinforcing effect (abrasion resistance and flex fatigue resistance).

The rubber compositions preferably contain carbon black, among the fillers, for improvement of the resulting tire in terms of abrasion resistance and flex fatigue resistance.

The nitrogen adsorption specific surface area ($N_2SA$) of carbon black is preferably 50 $m^2/g$ or greater, and more preferably 90 $m^2/g$ or greater. If the $N_2SA$ is smaller than 50 $m^2/g$, the reinforcibility may be insufficient, resulting in insufficient abrasion resistance and insufficient flex fatigue resistance. The $N_2SA$ is preferably 180 $m^2/g$ or smaller, and more preferably 130 $m^2/g$ or smaller. Carbon black with an $N_2SA$ exceeding 180 $m^2/g$ tends to be difficult to disperse, resulting in poor fuel economy, abrasion resistance, and flex fatigue resistance.

The $N_2SA$ of carbon black can be determined in conformity with JIS K6217-2:2001.

The amount of carbon black per 100 parts by mass of the rubber component is preferably 5 parts by mass or more, and more preferably 15 parts by mass or more. Less than 5 parts by mass of carbon black may fail to give sufficient abrasion resistance and sufficient flex fatigue resistance. The amount is preferably 100 parts by mass or less, more preferably 70 parts by mass or less, and still more preferably 50 parts by mass or less. More than 100 parts by mass of carbon black tends to have poor dispersibility and thus deteriorate fuel economy, abrasion resistance, and flex fatigue resistance.

In addition to the above components, the rubber compositions for tires may appropriately contain other compounding agents usually used in the preparation of rubber compositions, such as silane coupling agents, oil, stearic acid, zinc oxide, wax, antioxidants, vulcanizing agents, and vulcanization accelerators.

The rubber compositions of the present invention may be prepared by conventionally known methods. For example, the rubber compositions may be prepared by methods including kneading the components using a rubber kneading device such as an open roll mill, a Banbury mixer, or an internal mixer, and then vulcanizing the mixture.

Moreover, the ratio between the biomass-derived monomer component and the petroleum-derived monomer component is appropriately chosen depending on the comprehensive environmental needs at the time of the preparation of the rubber compositions, including the biomass resource supply situation, the petroleum resource (e.g. petroleum-derived monomer component) supply situation, and/or market needs (e.g. the trend of competition with the demand for biomass resources as food), and the biomass-derived monomer component or a combination of the biomass-derived monomer component and the petroleum-derived monomer component is polymerized at the appropriately chosen ratio to form a biomass-derived rubber, whereby a biomass-derived rubber having performance that is equivalent to when conventional synthetic rubber is used can be prepared.

The tire components of the present invention may be prepared using the above rubber compositions by usual methods. Specifically, the unvulcanized rubber composition optionally mixed with various additives may be extruded according to the shape of a tire component (e.g. tread, sidewall, bead filler, chafer, or clinch), formed and heated and pressed in a vulcanizer to form a tire component.

The pneumatic tires of the present invention may be prepared using the above rubber compositions by usual methods. Specifically, the unvulcanized rubber composition optionally mixed with various additives may be extruded according to the shape of a tire component such as a tread, formed on a tire building machine by a usual method and assembled with other tire components to build an unvulcanized tire, which may then be heated and pressed in a vulcanizer to form a tire.

The pneumatic tires of the present invention can suitably be used as tires for passenger cars, tires for trucks and buses, tires for two-wheeled vehicles, race tires, and the like.

EXAMPLES

The present invention will be described in greater detail below by reference to, but not limited to, examples.

The butadienes and the polybutadiene rubbers prepared in the following preparation examples were evaluated by the methods mentioned below.
(pMC of Butadiene and Polybutadiene Rubber)

The pMC values of the butadienes and polybutadiene rubbers were determined by the following method in conformity with ASTM D6866-10.

A sample (butadiene or polybutadiene rubber) was burnt to generate carbon dioxide ($CO_2$), which was then purified through a vacuum line. Next, the purified carbon dioxide was reduced with hydrogen in the presence of an iron catalyst to generate graphite (C). Then, the obtained graphite was charged into a cathode (inner diameter: 1 mm) using a hand press. This cathode was put on a wheel and then mounted on a measurement system (a tandem accelerator-based system dedicated to $^{14}C$ AMS (NEC Corp.)). The measurement system measured $^{14}C$ content and $^{13}C$ content. Using oxalic acid from the National Bureau of Standards (National Institute of Standards and Technology (NIST)) as a standard sample, pMC (%), which indicates a biomass ratio, was calculated from the measured values. In the pMC calculation, the values were corrected with the $^{13}C$ content values.
(Cis Content of Polybutadiene Rubber)

Cis content was measured using an NMR device AV400 with data analysis software TOP SPIN 2.1 (BRUKER Corp.).
(Glass Transition Temperature (Tg) of Polybutadiene Rubber)

Glass transition temperature (Tg) was measured using an automatic differential scanning calorimeter (DSC-60A, Shimadzu Corp.) at a temperature increase rate of 10° C./min in conformity with JIS K7121.
(Molecular Weight Distribution (Mw/Mn) of Polybutadiene Rubber)

Weight average molecular weight (Mw) and number average molecular weight (Mn) were measured by gel permeation chromatography (GPC) in the following conditions (1) to (8). Then the molecular weight distribution (Mw/Mn) of the polymers was calculated from the measured Mw and Mn values.
(1) Device: HLC-8020 from TOSOH CORP.
(2) Separation column: two GMH-XL columns in series from TOSOH CORP.
(3) Measurement temperature: 40° C.
(4) Carrier: tetrahydrofuran
(5) Flow rate: 0.6 mL/min.
(6) Injection amount: 5 μL
(7) Detector: differential refractometer
(8) Molecular weight standards: polystyrene standards Preparation Example 1 (Preparation of Butadiene from Butanol)

<Preparation of Biobutanol>

A 300-ml fermenter (DASGIP) was filled with 250 ml of a synthetic medium (containing saccharides) of Soni et al. (Soni et al., Appl. Microbiol. Biotechnol., 1987, vol. 27, pp. 1-5), and then sparged with nitrogen for 30 minutes. Then, *Clostridium acetobutylicum* (ATCC 824) was anaerobically inoculated on the medium. The culturing temperature was maintained at constant 35° C., and the pH was adjusted to 5.5 using a $NH_4OH$ solution. The anaerobic conditions were maintained during the culturing, and the shaking speed was maintained at 300 rpm. After five-day culturing, the culture fluid was distilled and then separated by a conventionally well-known ion exchange resin technique, thereby providing biobutanol (1-butanol).
<Preparation of Butadiene from Biobutanol>

Using a system shown in FIG. 1, biomass-derived butadiene was synthesized from the biobutanol (1-butanol) prepared in <Preparation of biobutanol>.

The system here (see FIG. 1) was provided with an alcohol feed pipe (material feed pipe) 21, a heater (electric furnace) 22 for vaporizing the fed alcohol, a dehydration column 23 for effecting dehydration reaction of the alcohol, a cooler 24 for cooling the product of the dehydration reaction and removing water from the purified alkene mixture, a heater 25 for vaporizing the alkene, a second reaction column 26 for further effecting dehydrogenation reaction of the alkene to synthesize butadiene, and a cooler 27 for collecting the generated reaction product. The dehydration column 23 was packed with 10 g of aluminum oxide (101095100, Merck) as catalyst.

The catalyst for the second dehydrogenation reaction was prepared as follows. Chromium nitrate (5.8 g) was dissolved in ion-exchange water. Then, SSZ-35 zeolite (6 g, silica/alumina ratio: 40) was put into and impregnated with the solution and left to stand overnight. Subsequently, the product was dried in a 100° C. oven to give a precursor. This precursor was put in a ceramic container and then fired for three hours at 700° C. in the air, thereby providing a chromium-supported zeolite catalyst containing 10% by mass of chromium.

Then, the second reaction column 26 was packed with 10 g of the chromium-supported zeolite catalyst.

Nitrogen gas was supplied to the dehydration column 23 through a gas feed pipe (not shown). The nitrogen gas was supplied at a LHSV rate of 1/hr. After the dehydration column 23 was heated to a predetermined temperature with the heater 22, a predetermined amount of the biobutanol was supplied through the alcohol feed pipe 21. The reaction conditions were as follows: reaction temperature was 500° C., reaction pressure was atmospheric pressure, and molar ratio of biobutanol to nitrogen was 50/50 (biobutanol/nitrogen). The reaction time was two hours. The resulting product was collected in the cooler (product trap) 24 connected to the dehydration column 23, and water was then separated away.

The second reaction column 26 was heated to 500° C. The cooler (product trap) 27 was cooled down to −20° C. A pre-heated gas mixture ((the butene mixture obtained in the first dehydration reaction)/(nitrogen)/(air)=1:1:1) was fed at a LHSV supply rate of 1/hr through the cooler (product trap) 24. The resulting reaction mixture was separated and purified by the method disclosed in JP 560-115532 A to give biomass-derived butadiene at a yield of 8%. The pMC value, which indicates the biomass ratio, of the obtained butadiene (biomass-derived butadiene) was 105%.

Preparation Example 2 (Preparation of Butadiene from Bioethanol)

Using the system shown in FIG. 1, biomass-derived butadiene was synthesized from a commercially available bioethanol by a conventionally known method of converting ethanol into butadiene (Kirshenbaum, I., "Butadiene", Encyclopedia of Chemical Technology, 3rd ed., vol. 4, Grayson, M., (ed.), John Wiley & Sons, New York, 1978, pp. 313-337). The pMC value, which indicates the biomass ratio, of the obtained butadiene (biomass-derived butadiene) was 108%.

Preparation Example 3 (Preparation of Butadiene from Bioethylene)

A catalyst prepared by dissolving 0.5 mmol/L of palladium acetate in 0.3 mol/L of $Na_3H_3PMo_9V_3O_{40}$ was introduced into the second reaction column 26 of the system shown in FIG. 1, and the system was purged with argon. Then a biomass-derived ethylene (trial product formed from corn-derived bioethanol) was fed into the system. A reaction was allowed to proceed for one hour while the catalyst solution was circulated in the system through a circulation line 28 at 150° C. and 0.5 MpaG. After the catalyst solution was removed through a drain of the cooler 27, an alumina catalyst (alumina KHA-46 from Sumitomo Chemical Co., Ltd.) immersed with bioethanol was put therein and a reaction was allowed to proceed at 400° C. for five hours. The reaction mixture was analyzed by GC/MS to confirm the generation of butadiene. The pMC value, which indicates the biomass ratio, of the obtained butadiene (biomass-derived butadiene) was 109%.

Preparation Example 4 (Preparation of Butadiene from Tiglic Acid)

An argon-filled autoclave was charged with 500 mg of tiglic acid (an intermediate of an amino acid-mediated in-vivo reaction) separated and purified from croton oil, 30 mg of tetrakis(triphenylphosphine)palladium(0), and 10 mg of triethylboron, and the contents were reacted at 200° C. for one hour. The resulting product was analyzed by GC/MS to confirm the generation of butadiene. The pMC value, which indicates the biomass ratio, of the obtained butadiene (biomass-derived butadiene) was 108%.

The biomass-derived butadienes prepared in Preparation Examples 1 to 4 were analyzed using an NMR device AV400 (with data analysis software TOP SPIN 2.1) from BRUKER Corp. to confirm these butadienes to be 1,3-butadiene.

Preparation Example 5 (Preparation of Biomass Polybutadiene Rubber (BBR))

The biomass-derived butadienes (1,3-butadienes) prepared in Preparation Examples 1 to 4 were mixed and the mixture was used as a monomer component to synthesize BBR (corresponding to the biomass-derived rubber in the present invention).

<Preparation of Catalyst>

A solution of neodymium octanoate (0.09 mmol) in cyclohexane, a solution of methylaluminoxane (2.7 mmol) in toluene, diisobutylaluminum hydride (4.7 mmol) and a solution of silicon tetrachloride in cyclohexane (0.09 mmol) were reacted and aged with 1,3-butadiene (biomass-derived butadiene) in an amount five times as large as that of neodymium at 50° C. for 30 minutes.

<Synthesis of BBR>

A nitrogen-purged autoclave (inner capacity: 5 L) was charged with 2.4 kg of cyclohexane and 300 g of 1,3-butadiene (biomass-derived butadiene) in nitrogen atmosphere. The catalyst prepared in advance was added to the mixture and the polymerization reaction was allowed to proceed at 50° C. for 30 minutes.

After the polymerization, a methanol solution of 0.3 g of 2,4-di-t-butyl-p-cresol was added and the solvents were removed, followed by drying to yield 250 g of biomass polybutadiene rubber (BBR). The pMC value, which indicates the biomass ratio, the Tg value, the cis content, and the Mw/Mn value of the obtained BBR were 105%, −110° C., 99.0% by mass, and 2.1, respectively.

The chemicals used in the example and comparative examples are listed below.

BR: Nipol BR1220 from ZEON Corp.

BBR: biomass polybutadiene rubber prepared in Preparation Example 5 (corresponding to the biomass-derived rubber in the present invention)

NR: RSS#3 (Tg: −75° C.)

Carbon black: SEAST N220 ($N_2SA$: 114 $m^2/g$) from Mitsubishi Chemical Corp.

Silica: ULTRASIL VN3 (average primary particle size: 15 nm, $N_2SA$: 175 $m^2/g$) from EVONIK DEGUSSA Silane coupling agent: Si75 from EVONIK DEGUSSA Zinc oxide: zinc oxide #1 from MITSUI MINING & SMELTING CO., LTD.

Stearic acid: stearic acid TSUBAKI from NOF Corp.

Oil: PROCESS X-140 from JX Nippon Oil & Energy Corp.

Antioxidant: Antigene 6C (N-(1,3-dimethylbutyl)-N'-phenyl-p-phenylenediamine) from Sumitomo Chemical Co., Ltd.

Wax: SUNNOC N from Ouchi Shinko Chemical Industrial Co., Ltd.

Sulfur: sulfur powder from KARUIZAWA IOU K.K.

Vulcanization accelerator (1): NOCCELER CZ (N-cyclohexyl-2-benzothiazolylsulfenamide) from Ouchi Shinko Chemical Industrial Co., Ltd.

Vulcanization accelerator (2): NOCCELER D (N,N'-diphenylguanidine) from Ouchi Shinko Chemical Industrial Co., Ltd.

Example and Comparative Examples

The chemicals except the sulfur and vulcanization accelerators were kneaded with a 1.7-L Banbury mixer in accordance with each of the formulations shown in Table 1. Then the kneaded mixture was combined with the sulfur and vulcanization accelerators using an open roll mill to prepare an unvulcanized rubber composition. The obtained unvulcanized rubber composition was then press-vulcanized using a 2 mm-thick mold at 170° C. for 15 minutes to prepare a vulcanized rubber composition (vulcanized rubber sheet).

The thus-prepared vulcanized rubber compositions were evaluated as follows. The results are shown in Table 1.

(1) Low-Temperature Hardness

Low-temperature hardness was measured at −10° C. using a type A durometer in conformity with JIS K6253.

The results are expressed as an index relative to that of Comparative Example 1 (=100). The lower the index is, the lower the hardness is, and, in turn, the better the low-temperature properties (e.g. grip performance on snow and grip performance on ice) are.

(2) Glass Transition Temperature (Tg)

The tan δ peak value of each composition was measured using a viscoelastic spectrometer VES (Iwamoto Seisakusho) over a temperature range from −100 to 100° C. at a dynamic strain of 0.5%. The measured values were defined as Tg values.

(3) Rolling Resistance Index

The tan δ of the compositions was measured using a viscoelastic spectrometer VES (Iwamoto Seisakusho) at a temperature of 70° C., an initial strain of 10%, and a dynamic strain of 2%. The measured values are expressed as an index calculated using the following equation, with the tan δ value of Comparative Example 1 being set equal to 100. The higher the index is, the better the rolling resistance (fuel economy) is.

(Rolling resistance index)=(tan δ of Comparative Example 1)/(tan δ of each composition)×100

(4) Flex Fatigue Resistance

A flex cracking test was performed in conformity with JIS K6260. In the test, samples were flexed five hundred thousand times, and the degree of cracking was then measured and expressed as an index based on the value of Comparative Example 1 (=100). The higher the index is, the better the flex fatigue resistance is.

(5) Abrasion Resistance

The amount of abrasion was measured using a Lambourn type abrasion tester at room temperature, a load of 1.0 kgf, and a slip rate of 30%. The values of the reciprocal of the amount of abrasion are expressed as an index based on the value of Comparative Example 1 (=100). The higher the index is, the better the abrasion resistance is.

TABLE 1

|  |  | Example 1 | Comparative Example 1 | Comparative Example 2 |
|---|---|---|---|---|
| Composition (parts by mass) | NR | 50 | 100 | 50 |
|  | BR | — | — | 50 |
|  | BBR | 50 | — | — |
|  | Carbon black | 30 | 30 | 30 |
|  | Silica | 30 | 30 | 30 |
|  | Silane coupling agent | 3 | 3 | 3 |
|  | Oil | 20 | 20 | 20 |
|  | Wax | 2 | 2 | 2 |
|  | Zinc oxide | 2 | 2 | 2 |
|  | Antioxidant | 2 | 2 | 2 |
|  | Stearic acid | 2 | 2 | 2 |
|  | Sulfur | 2 | 2 | 2 |
|  | Vulcanization accelerator (1) | 1 | 1 | 1 |
|  | Vulcanization accelerator (2) | 1.5 | 1.5 | 1.5 |
| Evaluation results | pMC of total rubber component | 105 | 105 | 53 |
|  | Low-temperature hardness | 78 | 100 | 80 |
|  | Tg (° C.) | −63 | −40 | −60 |
|  | Rolling resistance index | 70 | 100 | 75 |
|  | Flex fatigue resistance | 135 | 100 | 130 |
|  | Abrasion resistance | 125 | 100 | 120 |

As shown in Table 1, in Comparative Example 2 using the rubber component that contains 50% by mass of NR and 50% by mass of BR, good low-temperature properties, abrasion resistance, and flex fatigue resistance were exhibited, but the pMC of the total rubber component was low and did not sufficiently meet the demand for a sound material-cycle society. On the other hand, in Comparative Example 1 using the rubber component that contains 100% by mass of NR, the pMC of the total rubber component was high and met the demand for a sound material-cycle society, but greatly reduced low-temperature properties, abrasion resistance, and flex fatigue resistance were exhibited. In contrast, in Example 1 using the rubber component that contains 50% by mass of NR and 50% by mass of BBR, the pMC of the total rubber component was high and met the demand for a sound material-cycle society and, at the same time, good low-temperature properties, abrasion resistance, and flex fatigue resistance were exhibited. Table 1 also demonstrated that BBR is superior to BR in low-temperature properties, abrasion resistance, and flex fatigue resistance.

REFERENCE SIGNS LIST

21 Alcohol feed pipe (material feed pipe)
22 Heater (electric furnace)
23 Dehydration column
24 Cooler
25 Heater
26 Second reaction column
27 Cooler
28 Circulation line

The invention claimed is:

1. A method of producing a rubber composition for tires, comprising:
    a step (A) of preparing at least a first and second butadiene each formed separately by catalysis of at least one biomass-derived ingredient selected from the group consisting of biomass-derived ethanol, ethylene, and unsaturated carboxylic acids, wherein the first butadiene and second butadiene are formed from a different biomass-derived ingredient; and
    a step (B) of polymerizing at least the first and second butadiene prepared in the step (A) to prepare a biomass-derived polybutadiene rubber having a pMC (percent modern carbon) value of 1% or more as determined in conformity with ASTM D6866-10, and having a Tg (glass transition temperature) value of −120° C. to −80° C.,
    wherein, when the step (A) is a step of preparing butadiene by catalysis from ethylene, the step (A) comprises:
    partially converting ethylene into acetaldehyde using an oxidation catalyst, and
    forming butadiene by subjecting the acetaldehyde to a dehydration reaction with the remaining ethylene using a dehydration catalyst.

2. The method of producing a rubber composition for tires according to claim 1, wherein the at least one of the unsaturated carboxylic acids is at least one of tiglic acid and angelic acid.

3. A method of producing a tire component, comprising:
    a step (A) of preparing at least a first and second butadiene each formed separately by catalysis of at least one biomass-derived ingredient selected from the group consisting of biomass-derived ethanol, ethylene, and unsaturated carboxylic acids, wherein the first butadiene and second butadiene are formed from a different biomass-derived ingredient; and a step (B) of polymerizing at least the first and second butadiene prepared in the step (A) to prepare a biomass-derived polybutadiene rubber having a pMC (percent modern carbon) value of 1% or more as determined in conformity with ASTM D6866-10, and having a Tg (glass transition temperature) value of −120° C. to −80° C., wherein, when the step (A) is a step of preparing butadiene by catalysis from ethylene, the step (A) comprises:

partially converting ethylene into acetaldehyde using an oxidation catalyst, and forming butadiene by subjecting the acetaldehyde to a dehydration reaction with the remaining ethylene using a dehydration catalyst.

4. A method of producing a pneumatic tire, comprising:

a step (A) of preparing at least a first and a second butadiene each formed separately by catalysis of at least one biomass-derived ingredient selected from the group consisting of biomass-derived ethanol, ethylene, and unsaturated carboxylic acids, wherein the first and second butadiene are formed from a different biomass-derived ingredient; and a step (B) of polymerizing at least the first and second butadiene prepared in the step (A) to prepare a biomass-derived polybutadiene rubber having a pMC (percent modern carbon) value of 1% or more as determined in conformity with ASTM D6866-10, and having a Tg (glass transition temperature) value of −120° C. to −80° C., wherein, when the step (A) is a step of preparing butadiene by catalysis from ethylene, the step (A) comprises:

partially converting ethylene into acetaldehyde using an oxidation catalyst, and forming butadiene by subjecting the acetaldehyde to a dehydration reaction with the remaining ethylene using a dehydration catalyst.

5. The method of claim 1, wherein one of the at least one of the biomass derived ingredients is ethylene.

6. The method of claim 3, wherein one of the at least one of the biomass derived ingredients is ethylene.

7. The method of claim 4, wherein one of the at least one of the biomass derived ingredients is ethylene.

8. The method of claim 1, wherein preparing butadiene by catalysis comprises preparing butadiene by catalysis from biomass-derived butanol, ethanol, ethylene and tiglic acid.

9. The method of claim 3, wherein preparing butadiene by catalysis comprises preparing butadiene by catalysis from biomass-derived butanol, ethanol, ethylene and tiglic acid.

10. The method of claim 4, wherein the tire includes natural rubber and wherein preparing butadiene by catalysis further comprises preparing butadiene by catalysis from biomass-derived butanol, ethanol, ethylene and tiglic acid.

* * * * *